US00PP18089P2

(12) United States Plant Patent
Miyano

(10) Patent No.: US PP18,089 P2
(45) Date of Patent: Sep. 25, 2007

(54) ***PETUNIA* PLANT NAMED 'KEIWHIHUS'**

(50) Latin Name: ***Petunia hybrida* Vilm.**
Varietal Denomination: Keiwhihus

(75) Inventor: Shinya Miyano, Katori-gun (JP)

(73) Assignees: Keisei Rose Nurseries, Inc., Tokyo (JP); Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/409,911

(22) Filed: Apr. 24, 2006

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent Bell
*Assistant Examiner*—Annette H Para
(74) *Attorney, Agent, or Firm*—Jondle & Associates, P.C.

(57) ABSTRACT

A new *petunia* plant particularly distinguished by abundant, small, yellowish-white flowers, abundant branching with a great profusion of blooms, excellent tolerance to rain and a vigorous, decumbent growth habit is disclosed.

2 Drawing Sheets

Genus and species: *Petunia hybrida* Vilm.
Variety denomination: 'Keiwhihus'.

BACKGROUND OF THE NEW PLANT

The present invention comprises a new and distinct cultivar of *petunia,* botanically known as *Petunia hybrida* Vilm., and hereinafter referred to by the cultivar name 'Keiwhihus'. The new cultivar originated from a hybridization made in October 2000 in Katori, Chiba, Japan. The female parent was a proprietary unnamed *petunia* plant (unpatented), while the male parent was a different proprietary unnamed *petunia* plant (unpatented).

The new cultivar was created in 2000 in Katori, Chiba, Japan and has been asexually reproduced repeatedly by vegetative cuttings in Katori, Chiba, Japan. The present invention has been found to retain its distinctive characteristics through successive asexual propagations.

SUMMARY OF THE INVENTION

The following are the most outstanding and distinguishing characteristics of this new cultivar when grown under normal horticultural practices in Katori, Chiba, Japan.

A) Abundant, small, yellowish-white flowers;

B) Abundant branching with a great profusion of blooms;

C) Vigorous, decumbent growth habit;

D) Excellent tolerance to rain; and

E) Whole plant remains in bloom for a considerable period of time.

DESCRIPTION OF PHOTOGRAPHS

This new *petunia* plant is illustrated by the accompanying photographs which show blooms and foliage of the plant in full color, the colors shown being as true as can be reasonably obtained by conventional photographic procedures. The photographs are of a 2-month-old plant grown in a greenhouse in Katori, Chiba, Japan.

DESCRIPTION OF THE NEW CULTIVAR

Figure 1:
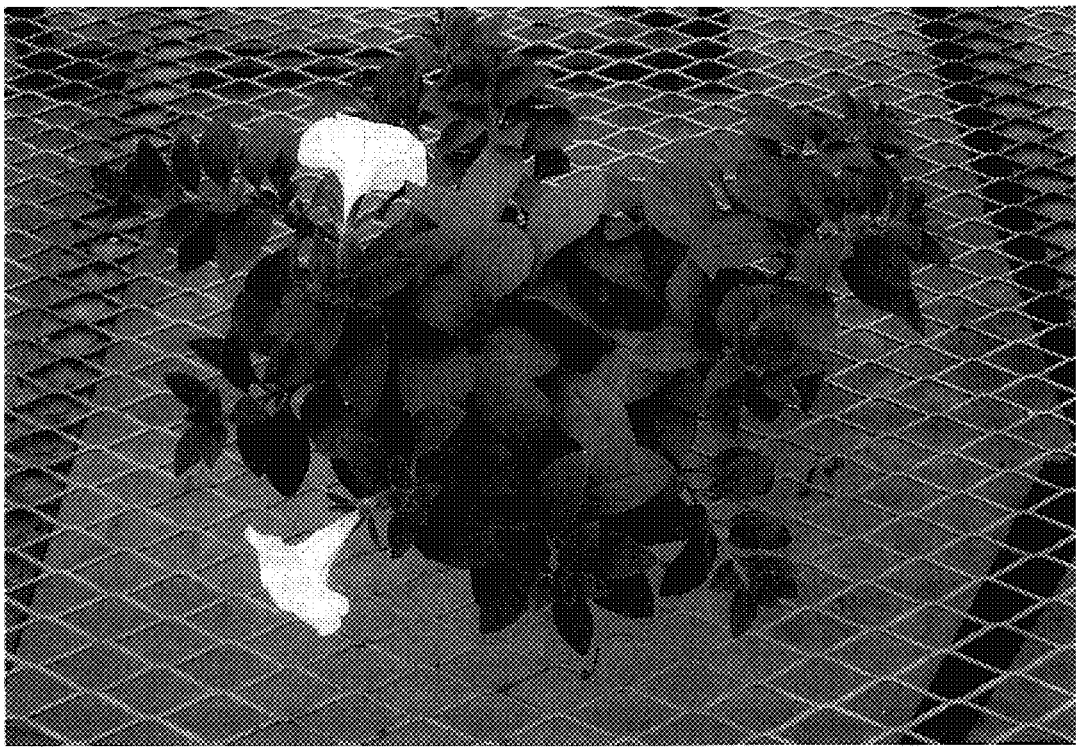
FIG. 1 shows the overall plant habit, including blooms, buds and foliage.
Figure 2:
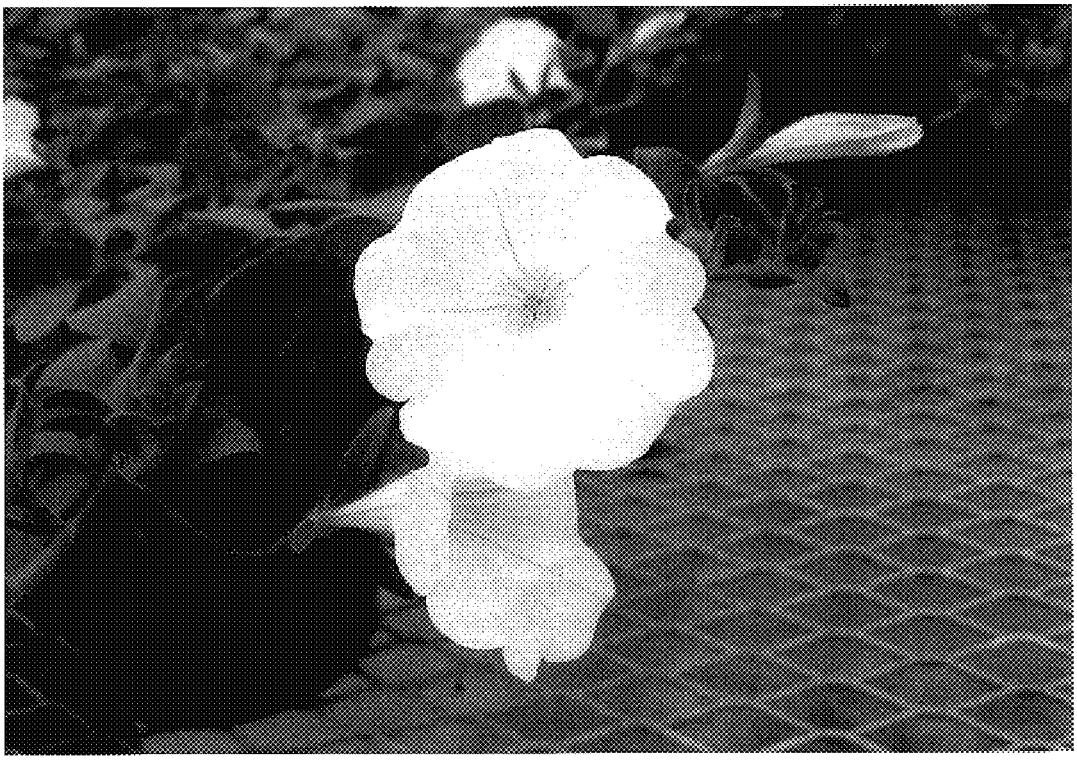
FIG. 2 shows the mature flower.

The following detailed description sets forth the distinctive characteristics of 'Keiwhihus'. The data which define these characteristics were collected from asexual reproductions carried out in Katori, Chiba, Japan. The plant history was taken on 2-month old plants which were planted as rooted cuttings in 12-cm pots in 2005 and grown in a greenhouse between 18° C. and 25° C. The plants were pinched once in September 2005. Observations were made when the plants were in full flower in October 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Solanaceae.
- *Botanical.*—*Petunia hybrida* Vilm.
- *Common name.*—*Petunia.*

Parentage:
- *Female parent.*—An unnamed proprietary white (RHS 155D) flowered *petunia* plant (unpatented).
- *Male parent.*—An unnamed proprietary white (RHS 155B) flowered *petunia* plant (unpatented).

Growth:
- *Form.*—Annual.
- *Habit.*—Decumbent to trailing shape, freely branching, vigorous.
- *Height* (*measured from the top of the soil*).—8.0 cm.
- *Diameter or area of spread.*—30.0 cm.
- *Propagation.*—Terminal tips for cutting.
- *Time to produce a finished flowering plant.*—2 to 3 weeks, in late April to late October, for a 12-cm pot.
- *Keeping quality.*—210 days.
- *Outdoor plant performance.*—Use in hanging baskets and containers; ground cover; excellent tolerance to rain; normal tolerance to wind.
- *Time to initiate and develop roots.*—7 days at 20° C. to 25° C.
- *Time to produce rooted cutting or liner* (*young plant*).—21 days at 20° C. to 25° C.

*Root description.*—Light brown, fibrous, fine; fleshy, freely-branching.

Branches:

*Number of branches.*—Many lateral branches.

*Length of lateral branches.*—15.0 cm.

*Diameter of lateral branches.*—0.2 cm.

Stems:

*Description.*—Round in cross-section.

*Aspect.*—Lying flat and apex ascended.

*Color.*—RHS 144B.

*Diameter.*—0.2 cm.

*Stem length.*—15.0 cm.

*Internode length.*—2.5 cm.

*Anthocyanin.*—Absent.

*Texture.*—Pubescent.

Leaves:

*Arrangement.*—Alternate, single leaves, abundant.

*Apex.*—Obtuse.

*Base.*—Cuneate.

*Color (mature leaves).*—Upper surface: RHS 137B. Lower surface: RHS 137C.

*Color (immature leaves).*—Upper surface: RHS 137B. Lower surface: RHS 137C.

*Margin.*—Entire.

*Size.*—Length: 4.0 cm. Width: 2.0 cm.

*Shape.*—Elliptical.

*Texture.*—Viscid, pubescence on both sides.

*Venation type.*—Reticulate.

*Petiole.*—Not clearly distinct from the leaf blade.

Flower buds:

*Color.*—RHS 160C.

*Shape.*—Cylindrical.

*Size.*—Length: 1.5 cm. Diameter: 0.5 cm.

Inflorescence:

*Blooming habit.*—Continuous.

*Inflorescence type.*—Single flower; self-cleaning.

*Arrangement.*—Borne in upper leaf axils.

*Aspect.*—Upright to outward.

*Shape.*—Funnel-shape with five lobes; petals fused.

*Fragrance.*—Faint.

*Flower number (per inflorescence).*—One.

*Quantity of flowers and buds per plant.*—Abundant.

*Flower longevity on plant.*—4 days.

*Peduncle.*—Color: RHS 144B. Length: 1.5 cm. Diameter: 0.1 cm. Texture: Pubescent, viscid.

Flowers:

*Size.*—Height (flower depth): 3.5 cm. Diameter: 4.5 cm.

*Corolla.*—Shape: Tube. Color (outside): RHS 158D with RHS 151A venation.

*Petals.*—Shape: Very broadly obtrullate. Size: Length (from the throat): 3.0 cm. Width: 1.5 cm. Apex: Cuspidate. Base: Fused. Margin: Entire, weakly undulated. Color (when opening): Upper surface: RHS 158D. Lower surface: RHS 158D. Color (fully opened): Upper surface: RHS 158D. Lower surface: RHS 158D. Throat color (inside): RHS 158D with RHS 151A venation. Petal texture: Upper surface: Satiny. Lower surface: Satiny.

*Calyx.*—Form: Tubular, star-shaped. Length: 1.0 cm. Diameter: 2.0 cm.

*Sepals.*—Number: 5. Shape: Narrowly oblong, bent over outwardly. Apex: Round. Base: Fused. Margin: Entire. Size: Length: 1.0 cm. Width: 0.3 cm. Color (mature): Upper surface: RHS 144B. Lower surface: RHS 144B. Color (immature): Upper surface: RHS 144B. Lower surface: RHS 144B.

Reproductive organs:

*Stamens.*—Quantity: 5. Anther: Shape: Ellipsoidal. Size: Length: 0.2 cm. Width: 0.1 cm. Color: RHS 13D.

*Pollen.*—Amount: Normal. Color: RHS 13D.

*Pistil.*—Quantity: One. Length: 1.5 cm.

*Style.*—Length: 1.0 cm. Color: RHS 154D.

*Stigma.*—Shape: Transversely elliptic. Color: RHS 144C.

*Ovary color.*—RHS 143C.

Fruit and seed set: A few seeds develop that are 0.05 cm in diameter and RHS 200A in color.

Disease and insect resistance: No particular resistance or susceptibility to diseases or insects noted to date.

COMPARISON WITH PARENTAL AND COMMERCIAL CULTIVARS

'Keiwhihus' differs from the female parent, an unnamed proprietary *petunia* plant (unpatented), by having a decumbent plant habit, while the female parent has a spreading plant habit. Additionally, 'Keiwhihus' has a shorter plant height and a smaller flower diameter than the female parent.

'Keiwhihus' differs from the male parent, an unnamed proprietary *petunia* plant (unpatented), by having a taller plant height, a larger flower diameter, and a larger plant diameter, than the male parent.

'Keiwhihus' is similar to the commercial variety 'Revolution White' (U.S. Plant Pat. No. 8,768) however, there are differences as listed in Table 1 below:

TABLE 1

Comparison of Characteristics between 'Keiwhihus' and 'Revolution White'

| Characteristic | 'Keiwhihus' | 'Revolution White' |
|---|---|---|
| Blooming period | Late April to late October in Japan | Late March to late September in Japan |
| Inside color of throat | RHS 158D with RHS 151A venation | RHS 155D with RHS 186A venation |
| Main color of corolla tube (outside) | RHS 158D | RHS 155D |
| Flower diameter | 4.5 cm | 7.5 cm |
| Plant height | 8.0 cm | 15.0 cm |
| Leaf length | 4.0 cm | 6.0 cm |
| Leaf width | 2.0 cm | 3.5 cm |
| Flower bud length | 1.5 cm | 3.5 cm |
| Flower bud diameter | 0.5 cm | 1.5 cm |
| Flower diameter | 4.5 cm | 7.5 cm |
| Petal color (when opening) | Upper surface: RHS 158D Lower surface: RHS 158D | Upper surface: RHS 155D Lower surface: RHS 155D |
| Petal color (fully opened) | Upper surface: RHS 158D Lower surface: RHS 158D | Upper surface: RHS 155D Lower surface: RHS 155D |
| Peduncle length | 1.5 cm | 2.0 cm |

I claim:

1. A new and distinct cultivar of *petunia* plant named 'Keiwhihus' as described and shown herein.

* * * * *